United States Patent [19]

Toth

[11] Patent Number: 4,858,619
[45] Date of Patent: Aug. 22, 1989

[54] INTRACRANIAL PRESSURE MONITORING SYSTEM

[76] Inventor: Marie A. Toth, 1462 Village Green Dr., Clairton, Pa. 15025

[21] Appl. No.: 67,984

[22] Filed: Jun. 29, 1987

[51] Int. Cl.⁴ ............................................... A61B 5/00
[52] U.S. Cl. .................................... 128/748; 604/247
[58] Field of Search .................. 128/748, 672–673, 128/674–675; 604/246–247, 253, 8–10

[56] References Cited

U.S. PATENT DOCUMENTS

| | | | |
|---|---|---|---|
| 3,157,201 | 11/1964 | Littmann | 128/675 X |
| 3,526,218 | 9/1970 | Reiss et al. | 128/748 |
| 3,581,733 | 6/1971 | Grandjean | 128/673 |
| 3,920,002 | 11/1975 | Dye et al. | 128/748 |
| 3,957,050 | 5/1976 | Hines, Jr. | |
| 4,072,146 | 2/1978 | Howes | 128/674 |
| 4,342,218 | 8/1982 | Fox | 128/673 X |
| 4,500,311 | 2/1985 | Redmond et al. | 604/246 |
| 4,621,647 | 11/1986 | Loveland | 128/748 |
| 4,648,868 | 3/1987 | Hardwick et al. | 128/675 X |
| 4,675,003 | 6/1987 | Hooven | 604/247 X |
| 4,714,458 | 12/1987 | Hooven | 604/247 X |

OTHER PUBLICATIONS

Nursing Photobook—Using Monitors, 1981, pp. 14–19, 24–37.

*Primary Examiner*—Kyle L. Howell
*Assistant Examiner*—Angela D. Sykes
*Attorney, Agent, or Firm*—Kirkpatrick & Lockhart

[57] ABSTRACT

A first valve has a first input port and first and second output ports with the first output port adapted for connection to a drainage collection bag. A tube connects the input port of the first valve to a patient. A second valve has an input port connected to the second output port of the first valve. A dome member has a first opening for connection with an output port of the second valve, a second opening for receiving a pressure transducer, and a third opening for permitting balancing of the system. Through this configuration, the drainage collection bag is located before the pressure sensor, but at a maximum distance from the patient to reduce the risk of infection. An automatic relief valve may replace the second valve to provide for automatic venting of dangerously high levels of intracranial fluids.

9 Claims, 2 Drawing Sheets

INTRACRANIAL PRESSURE MONITORING SYSTEM

BACKGROUND OF THE INVENTION

1. Field of the Invention

The present invention is directed to medical systems used for monitoring pressure while at the same time permitting drainage of bodily fluids, and more particularly to a system for monitoring intracranial pressure while allowing for the drainage of intracranial fluid.

The measurement of intracranial pressure (ICP) is increasingly used in the management of nuerological and nuerosurgical conditions. A high ICP can result in decreases in the level of consciousness, cerebal blood flow, and cerebal oxygenation. High ICP can also cause shifting of the brainstem, collapsing of the ventricles and, if unrelieved, brain death. Increased ICP occurs as a result of brain blood and cerebral spinal fluid being contained in a non-compliant structure called the cranial vault. An increase in one of these components causes a direct decrease in the other components to compensate.

ICP monitoring enables medical personnel to take life saving measures to counteract or decrease ICP before permanent damage can occur. ICP monitoring is achieved through a specially designed pressure tubing used to connect a pressure transducer to an intracranial access. Intracranial accesses include the intra-ventricular catheter, the subdural catheter, and the epidural catheter. The pressure tubing typically provides some means for allowing for the drainage of fluids.

An example of an external ventricular drainage assembly is disclosed in U.S. Pat. No. 4,500,311 to Redmond et al. The disclosed drainage assembly is used in conjunction with a ventricular drainage catheter. A valve is connected to the catheter for selectively opening and closing the external ventricular drainage assembly to fluid flow. The valve can also be used for connecting a transducer to the system. An adapter is connected to the valve for providing access to the fluid flow path. A one-way valve is connected to this adaptor. A length of flexible tubing is connected between the one-way valve and a drip chamber. The drip chamber is in communication with a collection reservoir.

Such a system places the collection reservoir beyond, or downstream, of the pressure sensor. It is known that the fluid drained from the brain may be contaminated with blood cells, brain tissue, or other matter. These materials may cause the pressure transducer to provide inaccurate readings. Such inaccurate readings can be extremely dangerous to the patient in that corrective action may be taken when none is necessary, or the need for corrective action not recognized.

There are other types of drainage systems, some of which provide for drainage before, or upstream, of the pressure transducer. For example, see pages 24 and 25 of the Nursing Photobook entitled "Using Monitors" (1981). When a system of the type using a subarachnoid screw is used, the collection reservoir is often placed too close to the patient thus increasing the risk of meningitis.

In prior art systems such as the system disclosed in U.S. Pat. No. 4,500,311, it is necessary for a nurse to physically open a valve to allow drainage to occur. Such manual manipulation is time consuming and allows for human error if the stop cocks are not returned to the proper position.

Other problems which have been encountered with various types of ICP monitoring systems include: Tubing connection points are often not secure and, should they come apart, rapid decompression of the brain results. When the tubing comes apart, it provides an opportunity for contamination of the system which ultimately contaminates the brain and it may allow for an influx of air which may result in an air emboli or pnuemocephalus.

It is often not known how much fluid has been removed.

There is no provision of a means for securely stabilizing the drainage unit at a prescribed gradient, or for preventing the unit from being accidentally dropped to the floor causing rapid decompression or from being raised above the balance level causing back flow of the contents into the brain, resulting in a higher ICP and contamination.

There is no provision of a means for irrigation, balancing, administering drugs, and the dwelling of medications without breaking the system or risking backflow into the brain.

With some systems there is no ability to determine the amount of fluid removed at any given interval. This results in the inability to trend patents or determine the need for continued ICP monitoring and/or venting or the need to incorporate additional aggressive measures.

Some systems do not provide for the collection of specimens or cultures without breaking the sterility of the system.

Most systems must be changed every twenty four hours to prevent infection. With each system change, there is the possibility of human error and/or contamination of the patient.

In view of the shortcomings of the ICP systems of the prior art, it is desirable to provide an Intracranial Monitoring System capable of providing the above-identified features while at the same time insuring that the pressure readings are as accurate as possible.

SUMMARY OF THE INVENTION

The present invention is directed to a system for monitoring intracranial pressure with a pressure transducer and draining intracranial fluid into a drainage collection bag. A first valve is provided which has an input port and first and second output ports. The first output port is adapted for connection to the drainage collection bag. A tube is provided for connecting the input port of the first valve to a patient. The tube has a length sufficient to reduce the risk of infection. A second valve is provided which has an input port connected to the second output port of the first valve, and an output port. A dome has a first opening for connection with the output port of the second valve, a second opening for receiving the pressure transducer, and a third opening for permitting balancing of the system.

According to one embodiment of the present invention, the angle between the first and second openings of the dome member is substantially 90 degrees.

The present invention is also directed to a method of assembling an intracranial pressure monitoring and drainage system. The method comprises the steps of connecting an input port of a first valve to a patient through a length of tubing. A drainage collection means is connected to an output port of the first valve. An input port of a second valve is connected directly to an output port of the first valve. A transducer is connected to an output port of the second valve.

The present invention also contemplates a valve arrangement used for connecting a patient to a pressure transducer and a drainage collection means where the drainage collection means is located between the patient and the pressure transducer. The valve arrangement is comprised of a first valve having an input port and first and second output ports, with the first output port adapted for connection to the drainage collection means. A tube is used for connecting the input port of the first valve to the patient. The tube has a sufficient length such that the drainage bag is a sufficient distance from the patient to reduce the risk of infection. A second valve has an input port directly connected to the second output port of the first valve, and an output port adapted for connection to the pressure transducer. Such a valve arrangement may be provided as an integral unit.

The present invention also contemplates an intracranial monitoring and automatic drainage system comprising a sensor and a tube for establishing a fluid path between the sensor and the patient. A relief valve is in communication with the fluid path. The valve is responsive to the pressure exerted by the fluid so as to automatically open to allow drainage.

The present invention is also directed to a method of monitoring intracranial pressure and automatically draining intracranial fluid. The method includes establishing a fluid path between a patient and a pressure sensor and connecting a relief valve to the fluid path. The valve is responsive to the pressure exerted by the fluid so as to automatically open to allow drainage.

The present invention sets forth numerous advantages over various prior art systems. These advantages include the ability to drain fluid from the brain before, or upstream, of the pressure sensor such that pressure readings are not affected by blood cells, brain tissue, or other matter in the fluid being drained. Most components of the present invention are currently already in most hospitals such that the system of the present invention can be easily set up and maintained. The embodiment of the present invention which allows for automatic drainage whenever the pressure exceeds a given setting allows for precise venting of pressure. Such venting occurs automatically without the need for human intervention. This provides immediate relief to the patient and eliminates the possibility of human error by an attendant leaving a stopcock in the wrong position. Even though the drainage collection bag is provided upstream of the pressure sensor, it is still provided at a substantial distance from the patient thereby decreasing the chances of infection. These and other advantages and benefits of the present invention will become apparent from the description of a preferred embodiment herein below.

DETAILED DESCRIPTION OF THE PREFERRED EMBODIMENTS

Figure 1:
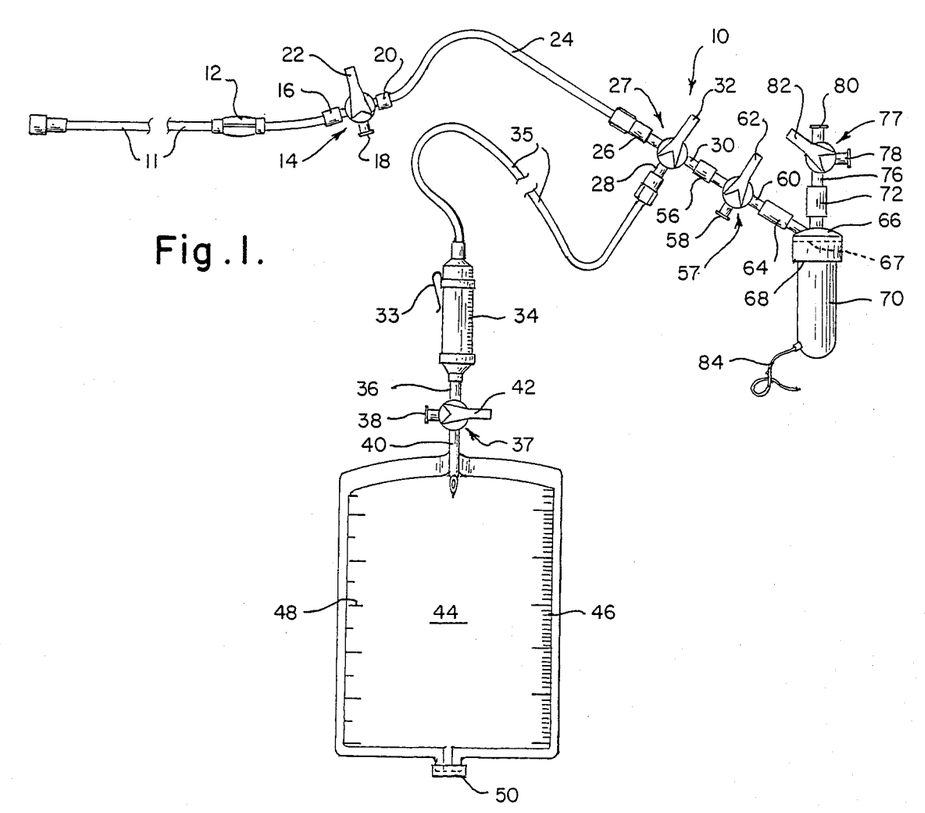
FIG. 1 illustrates the intracranial pressure monitoring and drainage system of the present invention.

Illustrated in FIG. 1 is an Intracranial Pressure Monitoring system 10 constructed according to the teachings of the present invention. The system 10 of the present invention can be used with various types of access devices such as an intra-ventricular catheter, subdural catheter, epidural catheter, or a subarachnoid screw (not shown). Those of ordinary skill in the art will recognize that the system 10 is capable of monitoring pressure and draining intracranial fluid without regard to the type of access device to which it is attached.

In FIG. 1, a first section of tubing 11 is provided which has an irrigation flash bulb 12. The irrigation flash bulb 12 is a known device which is commercially available. The first section of tubing 11 is connected through a secure type of connection, such as a Luer-Lok type of connector, to a first stopcock 14. The first stopcock 14 has an input port 16, a first output port 18, and a second output port 20. The stopcock 14 is provided with a control lever 22 which can be manipulated such that the input port 16 is in communication with the first output port 18, the input port 16 is in communication with the second output port 20, or the output ports 18 and 20 are in communication. The first stopcock 14 is a known three-way stopcock which is commercially available.

The second output port 20 of the first stopcock 14 is connected through a length of tubing 24 to an input port 26 of a second stopcock 27. The second stopcock 27 may be the same type of stopcock as the stopcock 14. The second stopcock 27 has a first output port 28, a second output port 30, and a control lever 32.

The first output port 28 of the stopcock 27 is connected to a calibrated drip chamber 34 through a length of tubing 35. The drip chamber 34 is calibrated in any appropriate units of volume for providing an indication of the volume of fluid drained from the brain through manipulation of the control lever 32. The drip chamber 34 has a small volume to provide an accurate reading of the amount of fluid drained. The drip chamber 34 carries a clamp 33 used to attach the drip chamber to an IV pole or the like.

The drip chamber 34 has an output port connecting to a first input port 36 of a third stopcock 37. The third stopcock 37 may be similar to the first and second stopcocks 14 and 27, respectively. The third stopcock 37 may have a first output port 38, a second output port 40, and a control lever 42.

The second output port 40 of the third stopcock 37 is connected to an input port of a drainage collection bag 44. The drainage collection bag has a much larger volume than the drip chamber 34 so that a substantial amount of fluid may be retained. The bag 44 is provided with calibrations 46 to indicate the amount of fluid contained within the bag 44. The drainage collection bag 44 may also be provided with linear measurements 48 to aid in the proper positioning of the system 10 as will be described in more detail hereinbelow in conjunction with FIG. 2. The bag 44 is also provided with a capped output port 50.

The second output port 30 of the stopcock 27 is connected directly to an input port 56 of a fourth stopcock 57. The fourth stopcock may be the same as the other stopcocks having a first output port 58, a second output port 60, and a control lever 62.

The second output port 60 of the stopcock 57 is connected to a first opening 64 in a dome member 66. The dome member 66 has a second opening 68 for receiving a pressure transducer 70. A flexible diaphragm 67 extends across the second opening 68. The dome member 66 has a third opening 72 connected to (an input port 76) of a fifth stopcock 77. The fifth stopcock 77 may be the same as the other stopcocks having a first output port 78, a second output port 80, and a control lever 82.

The dome member 66 may be a commercially available unit available from Gould. Similarly, the transducer 70 may be a commercially available unit such as the Gould P23ID. The transducer 70 produces an electrical signal available on conductor 84 which is representative of the intracranial pressure.

I. Operation Of The Present Invention

The present invention can be used to monitor intracranial pressure and drain intracranial fluid. Before the system 10 can be used, it is necessary to set up the system by filling the tubes 11 and 24, the stopcocks 14, 27, 57, and 77, as well as the sensor dome 66 with a saline solution. By filling the aforementioned components with saline solution, a fluid comunication path is established between the patient and the pressure transducer 70. Establishing such a fluid communication path is well known in the art. See, for example, the set up of various types of intracranial pressure monitoring systems set forth in pages 26 through 37 of the Nursing Photobook entitled "Using Monitors" (1981) which disclosure is hereby incorporated by reference.

Figure 2:
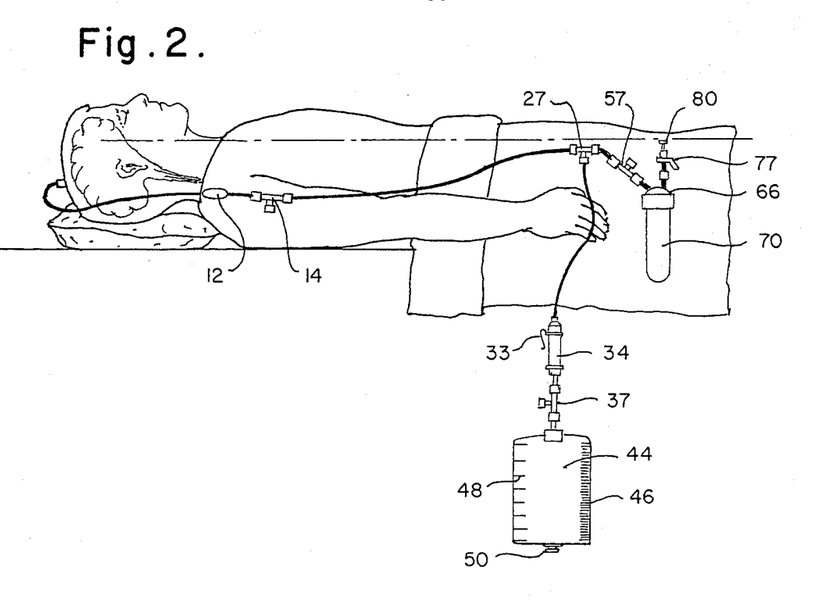
FIG. 2 illustrates proper positioning of the transducer to achieve balance.

After the aforementioned components have been filled with saline solution it is important for proper operation of any ICP monitoring system to be balanced. In the system illustrated in FIG. 1, the balancing port is the second output port 80 of the stopcock 77. In order for this system to be balanced, it is necessary to have the second output port 80 and the drip chamber 34 at the same level as the patient's foramen of Monro as shown in FIG. 2. That is, the top of the output port 80 and the drip chamber 34 are level with a point between the end of the patient's eyebrow and the tragus of the ear. When the second output port 80 and the drip chamber 34 are at the same level as the patient's foramen of Monro, the control lever 82 is actuated such that the input port 72 and second output port 80 of the stopcock 77 are in communication. This allows the saline solution above the flexible member 67 of the dome 66 to be exposed to atmosphere.

If it is desirable to move the drip chamber 34 either above or below this balance point to establish a pressure gradient, the linear scale 48 on the drainage bag 44 may be used to insure that the proper distance, either above or below the balance point, is established. The balancing of the present invention is not considered to be an important aspect of the present invention. The reader desiring more details regarding the details of intracranial pressure monitoring and drainage systems is referred to pages 14 through 19 of the aforementioned Photobook entitled "Using Monitors", the disclosure of which is hereby incorporated by reference.

After the system of the present invention has been properly set up and balanced, the elements set forth in FIG. 1 can be used as follows: With the input port 16 of the stopcock 14 in communication with the second output port 20, the input port 26 of the stopcock 27 in communication with the second output port 30, and the input port 56 of the stopcock 57 in communication with the second output port 60, the pressure exerted by the patient's brain is conveyed via the saline solution to the flexible diaphragm 67. The pressure transducer 70 is responsive to movements of the flexible diaphragm 67 such that electrical signals are produced on conductor 84 which are representative of the patient's intracranial pressure.

When it is desired to drain intracranial fluid, the control lever 32 of the stopcock 27 can be manually manipulated by an attendant in order to drain fluid from the tube 24 and hence reduce intracranial pressure. The amount of fluid drained can be easily read by using the graduations on the calibrated drip chamber 34. Whenever the drip chamber becomes too full, the stopcock 37 can be manipulated to empty the contents of the drip chamber 34 into the drainage collection bag 44. Because of the large volume of the drainage collection bag 44, the system of the present invention need not be changed as often as prior art systems. This results in reducing the chance of infection caused by frequent system changes. Additionally, fluid can be drained from bag 44 through output port 50 thereby reducing the need for changing the system.

One of the benefits of the ICP monitoring and drainage system 10 shown in FIG. 1 is that the drip chamber 34 and drainage collection bag 44 are located upstream of the pressure transducer 70. This reduces the possibility that blood cells, brain tissue, or other foreign matter will settle on the flexible member 67 thus impairing the ability of the pressure transducer 70 to provide accurate readings of intracranial pressure. Even though the drip chamber 34 and drainage collection bag 44 are provided upstream of the pressure transducer 70, they are still located a substantial distance from the patient. It is known that the pressure transducer 70 should not be more than four feet from the patient to insure accurate readings. Considering the length of the access device, for example, a catheter may be one foot long, the remaining lengths of tubing 11 and 24 are appropriately sized so that the drainage collection bag 44 is a maximum distance from the patient while keeping the pressure transducer 70 within four feet of the patient. This distance from the patient reduces the possibility of infection.

In the event that the access device becomes clogged, the irrigation flash bulb 12 can be used to flush fluid through the access device in an effort to unclog same. The present invention thus allows for irrigation of the access device without breaking the sterility of the system. The irrigation flash bulb 12 is an optional device. It is believed that aspects of the present invention can be practiced without using the irrigation flash bulb.

The first stopcock 14 can be used, via the first output port 18, to take samples of fluid or permit the dwelling of medications. The dwelling of medications entails attaching a medication delivery means (not shown) to the first output port 18 and leaving same attached for a period of time sufficient for the medication to defuse through the saline solution and enter the patient. The dwelling of medications and the taking of samples via the first output port 18 is considered to be an optional feature of the present invention. It is believed that other aspects of the present invention can be carried out without the first stopcock 14.

Another benefit of the ICP monitoring and drainage system 10 of the present invention stems from the fact that, because all the connections between the various components are secure types of connections, such as Luer-Lok connections, the system 10 of the present invention will not accidentally come apart during use.

II. Alternative Embodiments

According to one alternative embodiment of the present invention, the second stopcock 27 and fourth stopcock 57 may be provided as an integral unit. Such an integral unit eliminates some assembly steps thereby reducing the chances of human error, and eliminates a connection which is a possible point at which the system may come apart or become contaminated.

Figure 3:
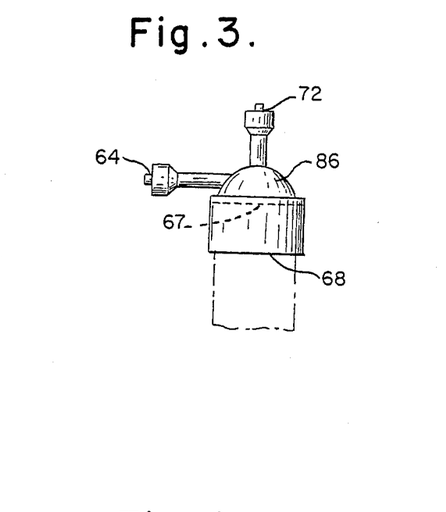
FIG. 3 illustrates a modified sensor dome.

According to another embodiment of the present invention, a modified sensor dome 86 is provided as shown in FIG. 3. The sensor dome 86 has a first opening 64 for connecting to the fourth stopcock 57, a second opening 68 for receiving the pressure transducer 70, and a third opening 72 for receiving the fifth, or balancing, stopcock 77. However, the angle between the first opening 64 and the second opening 68 has been changed from the obtuse angle found in the commercially available devices to a ninety degree angle. This change in angle helps to prevent blood cells, brain tissue, or other matter which is heavier than the saline solution from settling on the flexible member 67 of the sensor dome 86. The ninety degree angle facilitates the settling of foreign matter in those portions of the stopcocks and sensor dome between the second output port 30 of the second stopcock 27 and the flexible member 67. The settling of foreign matter in this area will not interfere with pressure readings as would the settling of foreign matter on the flexible member 67.

Figure 4:
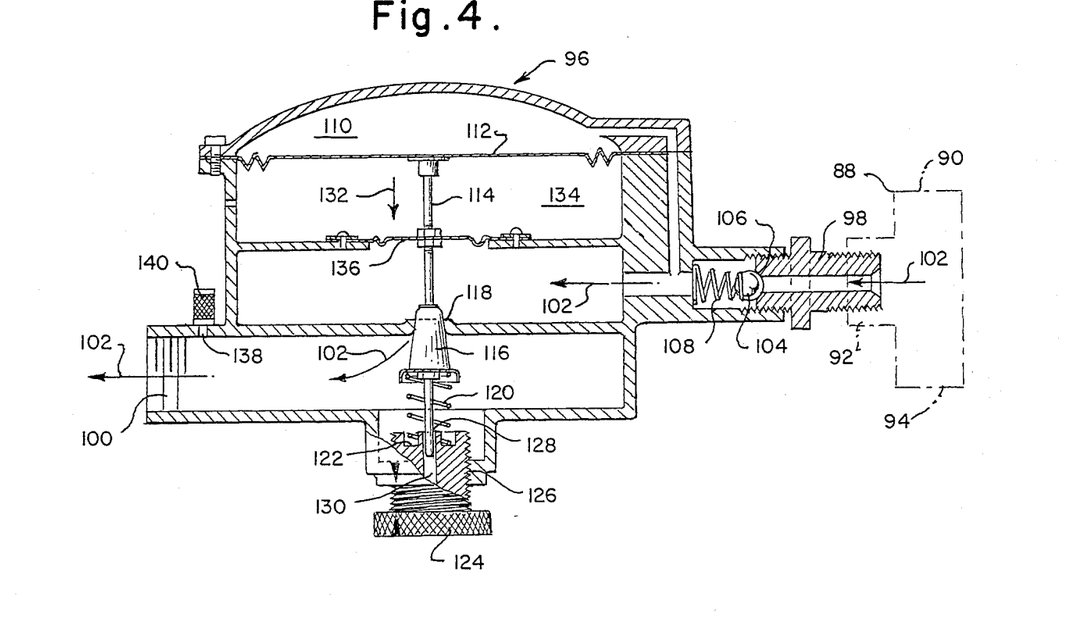
FIG. 4 illustrates an automatic relief valve which can be used in conjunction with the system illustrated in FIG. 1.

Another embodiment of the present invention anticipates replacing the second stopcock 27 with a T-shaped member 88 shown in FIG. 4. The T-member has an input port 90, a first output port 92, and a second output port 94. The first output port 92 communicates with an input port 98 of a one-way pressure relief valve 96. The one-way pressure relief valve 96 allows intracranial pressure to be automatically vented whenever dangerous levels are achieved. This is automatically done and does not require the intervention of an attendant. Thus, a nurse or other attendant is able to concentrate on the patient or the pressure monitor without worrying about manually opening a stopcock to vent intracranial pressure.

The one way pressure relief valve 96 establishes a fluid flow path as illustrated by the arrows 102 between the input port 98 and an output port 100. The input port 98 and output port 100 are provided with appropriate threads to enable a secure connection with the first output port 92 of the T-shaped member 88 and the input port of the calibrated drip chamber 34, respectively.

The input port 98 of the one way valve 96 carries a ball 104. The ball is held through the action of a spring 108 within a seat 106 formed in the input port 98. The spring 108, which has one end in contact with the ball 104 and the other end in contact with the housing of the valve 96, holds the ball 104 in the seat with a minimum of force. Any pressure exerted by the fluid in the direction of arrows 102 is sufficient to unseat the ball 104 to allow fluid to flow within the valve 96. However, any fluid which attempts to flow in a direction contrary to the arrows 102 will force the ball 104 into its seat 106 thereby preventing backflow of fluids.

The valve 96 includes a chamber 110 which is in communication with the fluid flow path illustrated by the arrows 102. One wall of the chamber 110 is comprised of a moveable diaphragm 112. The moveable diaphragm 112 experiences the same pressure which is exerted on the diaphragm 67 of the dome member 66, which is the pressure exerted by the fluids of the patient's brain.

The diaphragm 112 is connected to a piston 114. The piston 114 carries a conically shaped valve 116 which fits within a seat 118 formed in the relief valve's housing. The valve 116 is held in the seated position by a spring 120 which bears against a spring rest surface 122 formed on the end of a threaded thumb wheel 124. The threaded thumb wheel 124 is carried by threads 126 formed in the valve housing. The threaded thumb wheel 124 has a piston guide 128 formed therein as well as an empty space 130 to allow movement of the piston 114.

When the force exerted by the fluid in the chamber 110 upon the diaphragm 112 is sufficient to overcome the force of the spring 120, the diaphragm 112 and piston 114 move in a downward direction as shown by the arrow 132. Movement of the diaphragm 112 is facilitated by an empty chamber 134 which is vented to atmosphere. Fluid is prevented from entering the empty chamber 134 by a second moveable diaphragm 136 (having a much smaller surface area than the diaphragm 112) an o-ring (not shown) or the like. The downward movement of the piston 114, facilitated by the empty space 130, unseats the valve 116 from its valve seat 118 thereby allowing fluid to flow as indicated by the arrows 102.

The force required to unseat the valve 116 is dependent upon the strength of the spring 120 and its degree of compression. By screwing the threaded thumb wheel 124 into the valve housing, the spring rest surface 122 is raised thereby compressing the spring and increasing the force required to unseat the valve 116. By screwing the threaded thumb wheel 124 out of the valve housing, the spring rest surface 122 is lowered thereby decreasing the force required to unseat the valve 116. It is anticipated that the threaded thumb wheel 124 or the valve housing will be provided with graduations (not shown) so that the pressure at which venting occurs can be selected. It is also anticipated that the threaded thumb wheel 124 can be sufficiently screwed out of the valve housing such that virtually no force is required to unseat the valve 116. In this case, continual venting can be achieved.

The output port 100 may be provided with a relief vent 138. The relief vent 138, which is provided to prevent a vacuum from being formed behind the valve 116, may be provided with some type of filter 140 to prevent the escape of fluids.

It is anticipated that the valve 96 of the present invention will be made of clear material so that the springs 108 and 120, valves 104 and 116, and valve seats 106 and 118 can be visually inspected to determine if foreign matter is interfering with the proper operation of those components. It is also anticipated that the valve may be constructed of discrete components such that it may be taken apart and cleaned, or the springs replaced as needed. The springs 108 and 120 and ball 104 may be made of a stainless steel material.

SUMMARY

In summary, the present invention is for an intracranial pressure monitoring and drainage system. Depending upon the particular embodiment of the present invention which is used, the following benefits may be obtained.

The components which comprise the present invention are connected together through secure connections such as Luer-Lok connections. This prevents the system from coming apart which could result in rapid decompression of the brain. This also prevents contamination of the system and the influx of air which could result in an air emboli or pnuemocephalus.

Providing the optional flash bulb 12 at the proximal end of the tube 11 allows for irrigation of the access device without breaking the sterility of the system. The flash bulb may have a capacity, for example, of 0.5 cc which can be refilled under sterile conditions by way of the self-seal rubber comprising the flash bulb. This enables the irrigant to clear the access device of blood, brain, or clots that could potentially render the system useless or which would require immediate replacement of the access device.

The first stopcock 14 enables antibiotics, chemotherapy and irrigants to be introduced and dwelled without breaking the sterility of the system. Additionally, samples can be obtain through the first output port 18 without breaking the sterility of the system. By providing the option of carrying out these functions without breaking the sterility of the system, risk of patent infection is reduced.

By providing the T-shaped member 88 and the adjustable pressure regulating valve 96, once the system has been balanced to atmospheric pressure and the external auditory canal which is a representation of ventricular level, in accordance with the doctor's orders, a simple adjustment of the thumbwheel 124 allows fluid to be vented at all times. The valve automatically drains fluid from the brain until a desired level is achieved. This greatly reduces the amount of time needed to properly drain fluid and allows for immediate venting. The present invention therefore provides a system which allows immediate automatic venting of dangerously high pressures before the patient is adversely affected.

The present invention may be set up with an alarm system set below the venting pressure such that other measurements, for example, hyperventilation, osmotic diuresis, or sedation, can be done if indicated. Should it become necessary to vent fluids while a procedure is being done, such as suctioning of airways or placement of major vascular accesses, auto venting could be performed at this time to prevent sustained high ICP which otherwise would go unrelieved until the procedure is completed.

Backflow is often a serious problem incurred as the result of unknowing personnel working with the patient inadvertently lifting the drain bag 44 and drip chamber 34 above the level of the external auditory canal allowing fluid from the drainage bag 14 to be returned to the brain thereby causing contamination and an increased ICP. The anti-backflow device, i.e. spring 108 and ball 104, of the present invention prevents such accidents.

The calibrated drip chamber 34 may consist of a twenty cc capacity which enables the user to know exactly the amount of fluid vented at a given time. This allows for trends to be established to verify the need for continuing ICP monitoring and venting or the need for other aggressive or less aggressive therapy. The calibration would also allow for a time saving venting. For example, currently venting is done in a time frame of five seconds without knowing how much fluid is removed to return ICP to a desired level. Once a trend has been established for a patient, the amount of fluid in cc's can be removed at one time thereby returning ICP to acceptable levels. The calibrated drip chamber 34 also provides quick visual confirmation that the system is draining properly.

The clamp 33 fixed to calibrated drip chamber 34 allows the system 10 to be attached to an IV pole or other stationary unit to keep the gradient constant. This is important should the unit be used in the by-pass mode, i.e. thumbwheel 124 set to zero pressure for continuous venting, and to prevent the drainage unit from accidentally falling a large distance below the ventriculars thereby causing rapid decompression which could injure the brain and collapse the ventricals.

The calibrated drainage collection bag 44 may have a capacity of 600 cc's. This bag will collect the contents from the drip chamber for daily measurement of drained fluid. If larger sums are being drained, the bag 44 can be replaced with a standard transpak. The large capacity allows for enough average drainage of two to three days such that the system need not be changed as often as prior art systems. This reduces the risk of infection. The linear scale 48 is designed to give personnel a readily available measuring device for landmarks during the insertion of the monitoring catheter and for measuring gradient at which to drain fluid. A coupler (not shown) may be provided in the bas 44 to allow for random specimens to be removed at the furthest access point from the patient thereby decreasing risk of infection.

When the dome 86 shown in FIG. 3 is used, accurate monitoring can be achieved even when the discharge is bloody because the red blood cells, brain tissue, and other foreign matter do not have the force of gravity urging them toward the flexible member 67. Because this foreign material settles out before reaching the flexible member 67, distortion of the waveform is minimized.

It is possible to attach the pressure transducer 70 to an auto-regulating system which may be, for example, under computer control to establish trends.

While the present invention has been described with an exemplory embodiment thereof, it will be understood that many modifications and variations will be apparent to those of ordinary skill in the art. This disclosure in the following claims are intended to cover all such modifications and variations.

What is claim is:

1. A system for monitoring intracranial pressure and draining intracranial fluid comprising:
   a drainage collection means;
   first valve means having an input port and first and second output ports, said first output port being connected to said drainage collection means;
   tubing for connecting said input port of said first valve means to a patient, said tubing having a length sufficient to reduce the risk of infection;
   second valve means having an input port connected to said second output port of said first valve means, and an output port;
   a pressure transducer; and
   a dome member having a first opening connected to said output port of said second valve means, a second opening connected to said pressure transducer, and a third opening through which the system can be balanced;
   the system defining a fluid communication path between the patient and said pressure transducer wherein said pressure transducer and said dome member are in a downstream position along said path relative to said drainage collection means.

2. The system of claim 1 wherein the angle between said first and second openings of said dome member is substantially ninety degrees.

3. The system of claim 1 wherein said drainage collection means includes a calibrated drip chamber capable of providing an indication of the amount of fluid drained.

4. The system of claim 3 additionally comprising a calibrated collection bag connected to said drip chamber through a valve means such that the contents of said drip chamber can be periodically emptied into said collection bag.

5. The system of claim 1 additionally comprising an irrigation flash bulb means in-line with said tubing.

6. The system of claim 1 additionally comprising third value means located proximate to the patient, said third valve means having an input port and a first output port, both of which being in-line with said tubing, said third valve means having a second output port for one of taking samples and dwelling medications.

7. The system of claim 6 wherein said first, second and third valve means include first, second and third three port stopcocks.

8. The system of claim 1 wherein said first and second valve means are an integral unit.

9. The system of claim 1 wherein said first valve means is a relief valve responsive to the pressure exerted by the intracranial fluid so as to automatically open to drain the fluid into said drainage collection means.

* * * * *

UNITED STATES PATENT AND TRADEMARK OFFICE
CERTIFICATE OF CORRECTION

PATENT NO. : 4,858,619
DATED : August 22, 1989
INVENTOR(S) : Marie A. Toth

It is certified that error appears in the above-identified patent and that said Letters Patent is hereby corrected as shown below:

Col. 5, line 6, cancel "(an input port 76)" and substitute therefor --an input port 76--.

Col. 5, line 29, cancel "26through" and subsitute therefor --26 through--.

Col. 10, line 26, cancel "bas" and substitute therefor --bag--.

Signed and Sealed this

Twenty-fourth Day of July, 1990

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO.  : 4,858,619

DATED       : August 22, 1989

INVENTOR(S) : Marie A. Toth

It is certified that error appears in the above-identified patent and that said Letters Patent is hereby corrected as shown below:

Col. 2, line 27, delete "patents" and substitute therefor --patients--.

Col. 9, line 24, delete "patent" and substitute therefor --patient--.

Signed and Sealed this

Twenty-fifth Day of June, 1991

Attest:

HARRY F. MANBECK, JR.

Attesting Officer

Commissioner of Patents and Trademarks